United States Patent
Korb et al.

(10) Patent No.: US 11,213,551 B1
(45) Date of Patent: Jan. 4, 2022

(54) OCULAR TREATMENT COMPOSITIONS AND METHODS OF USE THEREOF

(71) Applicant: KORB RESEARCH, LLC., Boston, MA (US)

(72) Inventors: Donald R. Korb, Boston, MA (US); Karl F. Popp, Boston, MA (US); John A. Shipps, Boston, MA (US)

(73) Assignee: KORB RESEARCH, LLC., Boston, MA (US)

( * ) Notice: Subject to any disclaimer, the term of this patent is extended or adjusted under 35 U.S.C. 154(b) by 0 days.

(21) Appl. No.: 17/222,379

(22) Filed: Apr. 5, 2021

(51) Int. Cl.
| | | |
|---|---|---|
| *A61K 36/00* | (2006.01) | |
| *A61K 35/644* | (2015.01) | |
| *A61K 31/225* | (2006.01) | |
| *A61P 27/02* | (2006.01) | |
| *A61K 9/00* | (2006.01) | |
| *A61K 36/18* | (2006.01) | |

(52) U.S. Cl.
CPC .......... *A61K 35/644* (2013.01); *A61K 9/0014* (2013.01); *A61K 9/0048* (2013.01); *A61K 31/225* (2013.01); *A61K 36/18* (2013.01); *A61P 27/02* (2018.01)

(58) Field of Classification Search
CPC .............................. A61K 9/0048; A61P 27/02
See application file for complete search history.

(56) References Cited

U.S. PATENT DOCUMENTS

| | | | |
|---|---|---|---|
| 4,734,222 A | 3/1988 | Winterton et al. | |
| 5,371,108 A | 12/1994 | Korb et al. | |
| 8,084,047 B2 | 12/2011 | Shen et al. | |
| 8,455,016 B2 | 6/2013 | Maskin | |
| 8,906,427 B2 | 12/2014 | Maskin | |
| 9,526,763 B2 | 12/2016 | Rohloff et al. | |
| 10,328,025 B2 | 6/2019 | Ketelson et al. | |
| 10,537,608 B2 | 1/2020 | Shu | |
| 2005/0202097 A1 | 9/2005 | Maskin | |
| 2011/0294765 A1* | 12/2011 | Manzo | A61K 9/0014 514/167 |
| 2016/0051503 A1 | 2/2016 | Coffey | |
| 2019/0275022 A1 | 9/2019 | Dibas et al. | |
| 2019/0328753 A1 | 10/2019 | Yee | |
| 2019/0343848 A1 | 11/2019 | Rigas | |
| 2019/0374531 A1 | 12/2019 | Yang et al. | |
| 2020/0016084 A1 | 1/2020 | Ong | |
| 2020/0017619 A1 | 1/2020 | Fischer et al. | |

FOREIGN PATENT DOCUMENTS

WO   WO-2016070194 A1 *   5/2016   ............. A61K 33/04

OTHER PUBLICATIONS

Chan et al., "Update on the association between dry eye disease and meibomian gland dysfunction," Hong Kong Medical Journal, 2019.
Korb et al., "Evidence Suggesting that the Keratinized Portions of the Upper and Lower Lid Margins Do Not Make Complete Contact During Deliberate Blinking," Cornea, vol. 32, No. 4, 491-495, Apr. 2013.
Blackie et al., "A Novel Lid Seal Evaluation: The Korb-Blackie Light Test," Eye and Contact Lens, vol. 41, No. 2, 98-100, Mar. 2015.
Pult et al., "A new model of central lid margin apposition and tear film mixing spontaneous blinking," Contact Lens and Anterior Eye, 2015.

* cited by examiner

*Primary Examiner* — Qiuwen Ml
(74) *Attorney, Agent, or Firm* — Nath, Goldberg & Meyer; Joshua B. Goldberg; Nahied K. Usman

(57) ABSTRACT

A substantially water-free ocular treatment composition including about 20% to about 45% beeswax and about 20% to about 45% jojoba oil. The composition can include at least one ingredient selected from the group consisting of shea butter, caprylic/capric triglyceride, phospholipid, sodium hyaluronate, and coconut oil. The composition can be administered to a patient to improve the functionality of the tear film and decrease dry eye symptoms. The composition can be a semi-solid at room temperature and can liquefy when contacted with the skin at body temperature.

16 Claims, No Drawings

OCULAR TREATMENT COMPOSITIONS AND METHODS OF USE THEREOF

FIELD

The present subject matter relates to a composition for protecting ocular surfaces, and more particularly, to a composition for protecting ocular surfaces comprising a mixture of beeswax and jojoba oil.

BACKGROUND

Dry eye disease, also referred to as ocular surface disease, is an ophthalmic condition that typically results when the tear film is inadequate to protect the ocular surface. The tear film has three layers anchored to the corneal epithelium of the ocular surface: the lipid layer, the aqueous layer, and the mucin layer. Although the three layers are described as separate layers, it is generally accepted that there is some mixing of the various layers, particularly the mucin and aqueous layers.

The outermost layer is the lipid layer, reportedly varying in thickness from about 30 nm to about 150 nm. The lipid layer protects the underlying layers of the tear film and the corneal nociceptors of the neurosensory system. The aqueous layer is the middle layer and is reported to be about 2-4 microns thick. The mucin layer, the innermost layer, is anchored to and directly protects the epithelium of the ocular surfaces. The mucin layer is reported to be about 0.5-1.5 microns thick. The lipid layer primarily functions to retard evaporation of the aqueous layer. Dry eye disease can occur when the lipid layer fails to adequately minimize tear film evaporation and maintain homeostasis.

The lipids forming the lipid layer are primarily secreted by the meibomian glands. For the eye to achieve an optimal ocular surface protective system, the meibomian glands must function at a level of efficacy to provide adequate lipid levels to form and maintain the lipid layer, thereby minimizing tear film evaporation and maintaining homeostasis. Meibomian glands discharge lipids (sebum) onto the lid margin upon completion of a blink. In addition to facilitating secretion of lipids and other chemical constituents of the tear film, blinking spreads the tear film over the ocular surface, polishes the planar tear film for optimal vision, and acts as a pump system to remove a portion of the tear film through the nasal lacrimal system when needed. The movement of the lids and eyelashes also acts as a defense against intruding foreign material.

Meibomian gland dysfunction is an obstructive condition of the ducts of the meibomian glands that prevents the glands from discharging their lipid liquid secretions (sebum) to maintain the tear film and protect the ocular surface. Meibomian gland dysfunction is the leading cause of dry eye disease throughout the world. Properly functioning meibomian glands discharge sebum continuously primarily during the waking hours to provide a continuous feed system to maintain the tear film and protect the ocular surface. However, in almost all dry eye conditions, the meibomian glands do not work well and/or underperform.

In recent times, there has been a significant rise in occurrences of dry eye disease. One of the main causes of this rise is an overall increase in screen time. People staring at a screen for extended periods of time have a tendency to blink less. Reduced blinking leads to inadequate levels of lipid secretion and, consequently, a lipid layer that is inadequate to retard evaporation of the aqueous layer of the tear film.

An insufficient lipid layer also fails to protect the nociceptors of the neurosensory system from stimulus. The nociceptors are primarily protected by the tear film during waking hours. If the patient's tear film is not adequate, environmental factors, such as a wind current, may cause tearing. An optimally functioning tear film may protect ocular surfaces from winds that are up to about 4-5 miles per hour. When the tear film becomes compromised and the nociceptors are not protected, winds at this speed can cause the nociceptors to set off a cascade of neurosensory stimulation, resulting in symptoms of discomfort, inflammation, and mild to severe or even disabling sequelae, depending upon the individual situation.

Many conventional dry eye treatments fail to adequately protect the ocular surfaces and neurosensory systems. For example, many treatments have been directed to palliative measures, such as suppressing inflammation with steroids. Other treatments, such as lubricant eye drops, are severely limited by the minimal capacity of the eye to retain only about 1-3 microliters of additional substances from external sources. For example, a standard eye drop is about 30-50 microliters, while the eye has a capacity to retain only about 2-5 microliters. As a result, over 90% of a standard eyedrop overflows on to the face. Thus, much of the eyedrop is lost upon dispensing and any remaining amount stays in the eye for a very short time (minutes to at most an hour) before evaporating. These treatments fail to address the need to provide a reservoir to facilitate protection of the ocular surface and neurosensory systems for at least the majority of waking hours.

Accordingly, a composition for protecting the ocular tear film is needed.

SUMMARY

A composition for ocular treatment as described herein can be a substantially water-free composition including about 20% to about 45% beeswax and about 20% to about 45% jojoba oil. The composition can include at least one further ingredient/excipient. Such further ingredients/excipients can include any or all those selected from the group consisting of shea butter, caprylic/capric triglyceride, phospholipid, hyaluronic acid, and coconut oil, alone or in any combination of two or more thereof. The composition can be administered to a patient to decrease evaporation of moisture from the tear film and increase the thickness of the tear film. The composition can be a semi-solid at room temperature and can liquefy when contacted with the skin at body temperature. The composition can be administered to a patient for treating or preventing dry eye disease, meibomian gland dysfunction, or eyelid infection or inflammation. The composition can replicate or be adjunctive to the function and efficacy of those ingredients supplied by the secretory systems of an optimally functioning eye.

The composition can be administered to the patient by rubbing the composition on an external eyelid surface of a patient to create an oily reservoir thereon. The external eyelid surface can include the outer skin of the upper eyelid, the outer skin of the lower eyelid, the eyelid margin, and the eyelashes, or combinations of 2 or more thereof. The composition deposited on the external eyelid surface can move to the ocular surface in minute portions at a time, primarily by blinking. In this manner, a continuous feed of the composition is supplied to the ocular surface.

The composition can help prevent evaporation from the aqueous layer and provide a thicker tear film. The composition can provide an extended period of protection for the ocular surface and neurosensory systems without causing blurring of vision. For example, the composition can protect the ocular surfaces for about 10 hours to about 24 hours per day. The composition can protect the nociceptors from winds ranging from about 1 MPH to about 10-20 MPH. The composition can replicate or be adjunctive to the function and efficacy of those ingredients supplied by the secretory systems of an optimally functioning eye to protect the ocular surfaces for extended periods of time to withstand the contemporary demands and stresses of prolonged electronic screen viewing and other visual activities associated with reduced blinking.

It should be noted the compositions described herein may be regulated as a cosmetic, drug, device, medicament, or combinations thereof.

DETAILED DESCRIPTION

Definitions

The following definitions are provided for the purpose of understanding the present subject matter and for constructing the appended patent claims.

The phrase "ocular surface" refers to the eye anatomy that can be observed if the upper lid is raised and the lower lid lowered, including the inner surfaces of both upper and lower eyelids upon their eversion, but without surgical intervention, and the non-visible surfaces within the eye cavity.

The term "ophthalmic" refers to relating to the eye and its diseases.

The phrase "tear film" refers to the complex mixture of substances secreted from multiple sources, including the lacrimal gland, the accessory lacrimal glands, the meibomian glands, and the goblet cells, on to the ocular surface. The tear film resides on the ocular surface.

The phrase "lipid layer" refers to the outermost layer of the tear film. Typically, the lipid layer of the tear film will vary in thickness from about 30 nm to about 150 nm. The lipid layer primarily functions to retard evaporation at the lipid layer—air interface. The lipids forming the lipid layer are primarily secreted by the meibomian glands.

The phrase "aqueous layer" refers to the middle layer of the tear film and is the thickest layer of the tear film. Typically, the aqueous layer of the tear film will be about 2 microns to about 4 microns thick.

The phrase "mucin layer", also termed mucous, mucus, or glycocalyx, refers to the innermost layer of the tear film that is typically anchored to and protects the epithelium of the ocular surface. Typically, the mucin layer of the tear film is about 0.5 microns to about 1.5 microns thick.

The term "homeostasis" refers to the process of maintaining a stable, relatively constant function of the eye.

The phrase "substantially water-free" is intended to mean that the composition comprises the water content which would nominally be present in the ingredients. No water is added to the formulation. Total moisture content would be less than 5%, and more likely less than 1% on a weight basis.

The phrase "external eyelid surface" as used herein can include the outer skin of the upper eyelid, the outer skin of the lower eyelid, the eyelid margin, and the eyelashes, or combinations of 2 or more thereof. The composition deposited on the external eyelid surface can move to the ocular surface in minute portions at a time, primarily by blinking.

The phrase "eyelid margin" refers to the edge of the eyelid. Unlike the skin of the external eyelid surface, which includes keratinized non-wetting epithelium, the eyelid margin includes non-keratinized wetting epithelium. The junction of the wetting and non-wetting epithelium is termed the mucocutaneous junction. The orifices of the meibomian glands are located slightly in front of the mucocutaneous junction. The meibomian glands discharge their oil product (sebum) on to the keratinized wetting epithelium. A row of eyelashes extends along the front of the eyelid margin.

The phrase "meibomian glands" refers to "oil glands" located in the tarsal plates of the eyelids. The meibomian glands discharge an oily substance, sometimes referred to as the sebum or meibomian lipids, through their orifices on to the eyelid margin, primarily upon blinking. The oily substance is then moved from the eyelid margin by eye movements and eyelid actions to the lipid layer where it provides tear stabilization and serves as a barrier protector of the aqueous layer underneath.

The meibomian lipids form a thin, smooth film. The thickness and probably the composition of the film influence the rate of evaporation. The melting range of the meibomian lipids ensures sufficient fluidity for delivery to the tear film from the lid margin reservoirs, while the film itself may exhibit a higher viscosity at the cooler temperature of the ocular surface. The factors governing lipid film formation during the blink are not fully understood, but one view is that the polar lipids, interacting with the aqueous sub-phase of the tear film, spread in advance of the non-polar components, which form the bulk of the film. The meibomian lipids stabilize the tear film by lowering its free energy; they carry water into the film during its formation and interact with lipid-binding proteins in the aqueous phase, such as tear lipocalin. The lipocalins, complexed with other tear components, may also contribute to the high, non-Newtonian viscosity of the tear film and its low surface tension, features which are essential for tear film stability. Formation of the lipid film is a complex process. The lipid layer comes to a stop after completion of the blink and remains relatively immobile until it is compressed in the down-phase of the blink that follows. Then, it either retains its structure in a series of subsequent blinks or is re-constituted after mixing with the reservoir lipids. Delivery of meibomian lipid to the marginal reservoirs is mainly the result of continuous secretion, under neural and hormonal control, supplemented by lid action. The reservoirs provide a hydrophobic barrier to tear overspill and to contamination by skin lipids which might destabilize the tear film. They also provide a portion of the route for meibomian gland secretion to join the lipid layer.

The phrase "jojoba oil" refers to jojoba oil, jojoba wax, combinations thereof and/or derivatives thereof derived from the jojoba plant. The terms "jojoba oil" and "jojoba wax" are often used interchangeably because the wax visually appears to be a mobile oil, but as a wax it is composed almost entirely (~97%) of mono-esters of long-chain fatty acids and alcohols (wax ester), accompanied by only a tiny fraction of triglyceride esters. One such substance has been described by the PCPC (Personal Care Products Counsel) International Cosmetic Ingredient Dictionary and Handbook as *Simmondsia chinensis* (Jojoba) Seed Oil. Jojoba oil is non-aqueous and is typically used as a skin conditioning agent, an occlusive, and a hair conditioning agent.

The phrase "shea butter" refers to a triglyceride derived from the tree *Shorea stepnoptera*. It is rich in C18 unsaturated carbon length chain lengths. One such substance has been described by the PCPC (Personal Care Products Counsel) International Cosmetic Ingredient Dictionary and Handbook as *Butyrospermum parkii* (Shea) Butter. Shea butter is non-aqueous and is typically used as a skin conditioning agent, an occlusive, and a viscosity increasing agent.

The phrase "coconut oil" refers to a triglyceride derived predominately from the seed of *Cocos nucifera*. It is rich in carbon lengths below C18, and particularly C12 (lauric). One such substance has been described by the PCPC (Personal Care Products Counsel) International Cosmetic Ingredient Dictionary and Handbook as *Cocos nucifera* (Coconut) Oil.

The phrase "caprylic/capric triglyceride" is a mixed triglyceride derived predominately from kernel oils, e.g., coconut oil, palm kernel oil, and babassu oil. One such substance has been described by the PCPC (Personal Care Products Counsel) International Cosmetic Ingredient Dictionary and Handbook as caprylic/capric triglyceride. Caprylic/capric triglyceride is typically used as a skin conditioning agent and an occlusive.

The term "liquefy" refers to a process to soften, melt, disperse, or otherwise cause a loss of viscosity in a solid or semi-solid composition, rendering the composition more fluid.

The term "phospholipid" refers to an ingredient including a phospholipid. A preferred, non-limiting phospholipid containing ingredient useful in the present compositions is lecithin. Lecithin is typically used as a skin conditioning agent, an emulsifying agent, and a surfactant. Other phospholipid-containing ingredients known to those of ordinary skill in the art, such as those described in the resources below, are further contemplated as useful in the present compositions. The phospholipids can include at least one of neutral, anionic and cationic phospholipids. Other phospholipids well known to those of skill in the art as useful in topical and ophthalmic compositions are further contemplated as useful in the present compositions, such as those described in *The Merck Index*, Thirteenth Edition, Budavari et al., Eds., Merck & Co., Inc., Rahway, N.J. (2001); the PCPC (Personal Care Products Counsel) *International Cosmetic Ingredient Dictionary and Handbook*, On Line Infobase (2021); and the "Inactive Ingredient Guide", U.S. Food and Drug Administration (FDA) Center for Drug Evaluation and Research (CDER) Office of Management, January 2021, the contents of which are hereby incorporated by reference in their entirety.

The term "beeswax" refers to *Cera alba*, White Beeswax, Yellow Beeswax, or *Apis mellifera*, and is listed in pharmaceutical pharmacopoeias and cosmetic ingredient dictionaries such as those listed above. Beeswax is nonaqueous, includes about 15% free fatty acids, 15% hydrocarbon resins, and the balance esters. It is rich in carbon chain lengths greater than C18 and is typically used as a skin conditioning agent and a viscosity increasing agent-non-aqueous.

The phrase "degradation products" refers to the compositions produced by a change in the physical or chemical properties of one or more of the functional ingredients of the composition used according to the present methods. Degradation may result in the change in the physical appearance, physical attribute, or a loss of functionality of the ocular treatment composition. A product or composition which maintains sufficient physical appearance or chemical stability to render it functional for its intended use is considered storage stable.

The terms "patient" or "subject," are used interchangeably herein to refer to a mammal or animal, including but not limited to a human being.

It is noted that, as used in this specification and the appended claims, the singular forms "a", "an", and "the" include plural references unless the context clearly dictates otherwise.

Unless defined otherwise, all technical and scientific terms used herein have the same meaning as commonly understood to one of ordinary skill in the art to which the presently described subject matter pertains.

Where a range of values is provided, for example, concentration ranges, percentage ranges, or ratio ranges, it is understood that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the described subject matter, subject to any specifically excluded limit in the stated range. Where the stated range includes one or both of the limits, ranges excluding either or both of those included limits are also included in the described subject matter.

Throughout the application, descriptions of various embodiments use "comprising" language. However, it will be understood by one of skill in the art, that in some specific instances, an embodiment can alternatively be described using the language "consisting essentially of" or "consisting of".

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about". Accordingly, unless indicated to the contrary, the numerical parameters set forth in the following specification and attached claims are approximations that may vary depending upon the sought desired properties. At the very least, each numerical parameter should at least be construed in light of the number of reported significant digits and by applying ordinary rounding techniques.

The ocular treatment composition as described herein can be a substantially water-free composition including a first wax having a first melting temperature and a second wax having a second melting temperature different from the first melting temperature. Additional waxes may optionally be included in the composition as needed. A ratio of the first wax to the second wax can range from about 1:1 to about 2:1 in the composition. In an embodiment, a ratio of the first wax to the second wax can be about 1:1 in the composition. In an embodiment, the composition can include one or more oils, emollients, antimicrobials, antioxidants, and/or thickening agents. In an embodiment, the composition can include at least one ingredient selected from the group consisting of caprylic/capric triglyceride, phospholipid, coconut oil, and hyaluronic acid. In an embodiment, a combined concentration of the first wax and the second wax in the composition can range from about 40% to about 90%. In an embodiment, the composition can include from about 0% to about 16% shea butter. In an embodiment, the composition can include from about 5% to about 15% caprylic/capric triglyceride. In an embodiment, the composition can include from about 0.1% to about 2% phospholipid. In an embodiment, the composition can include 0.01% to about 0.1% sodium hyaluronate. In an embodiment, the composition can include from about 0% to about 16% coconut oil.

The composition can be administered to a patient to decrease evaporation from the tear film and increase the thickness of the tear film. The composition can be non-fluid at room temperature and liquefy when in contact with surfaces with elevated temperatures, such as the skin at body temperatures.

The compositions as described herein can liquefy upon application to the patient's external eyelid surface to ensure sufficient fluidity for delivery to the tear film from the application area, such as the eyelid margin, while the film itself may exhibit a higher viscosity at the cooler temperature of the ocular surface. The factors governing film formation are complex and may vary somewhat within and across patients. Naturally occurring ocular polar compositions interact during blinking with the aqueous sub-phase of the tear film, spread in advance of the non-polar components, which form the bulk of the tear film. The ocular treatment composition becomes dispersed in situ with the meibomian lipids. A dynamic process of blinking, mixing, reservoir release and replenishment, dispersion with naturally occurring substances in the eye, and formation of a mixture of chemical substances from natural and external sources ensues, resulting in the development of a complex film which protects and restores the functional ocular surface.

In an embodiment, the first melting temperature can be greater than 50° C. In an embodiment, the second melting temperature can be less than 20° C. In an embodiment, the first melting temperature can range from about 62° C. to about 64° C. In an embodiment, the second melting temperature can range from about 5° C. to about 11° C. In an embodiment, the first wax is beeswax. In an embodiment, the second wax is jojoba oil. Preferably, the first melting temperature is from beeswax and the second is from jojoba oil.

In an embodiment, the composition includes a third wax having a third melting temperature. The third melting temperature can be different from the first and second melting temperatures. The third melting temperature can range from about 31° C. to about 37° C. In an embodiment, the third wax is shea butter.

In an embodiment, the composition can include hyaluronic acid, a salt, ester or complex thereof. In an embodiment, the hyaluronic acid includes sodium hyaluronate. Sodium hyaluronate is typically used as a skin conditioning agent and a humectant.

In an embodiment, the composition can include one or more oils. Exemplary oils suitable for use in the composition include, but are not limited to, sunflower oil, coconut oil, castor oil, vegetable oil, corn oil, canola oil, soybean oil, olive oil, babassu oil, avocado oil, apricot oil, meadowfoam seed oil, macadamia seed oil, oat kernel oil, palm seed oil, safflower oil, sandalwood oil, sesame oil, sunflower oil, almond oil, wheat germ oil, cranberry seed oil, daikon seed oil, and combinations thereof. In an embodiment, the composition includes coconut oil (*Cocos nucifera*). Coconut oil is typically used as an occlusive and a hair conditioning agent. Other oils well known to those of skill in the art as useful in topical and ophthalmic compositions are further contemplated as useful in the present compositions, such as those described in *The Merck Index*, Thirteenth Edition, Budavari et al., Eds., Merck & Co., Inc., Rahway, N.J. (2001); the PCPC (Personal Care Products Counsel) *International Cosmetic Ingredient Dictionary and Handbook*, On Line Infobase (2021); and the "Inactive Ingredient Guide", U.S. Food and Drug Administration (FDA) Center for Drug Evaluation and Research (CDER) Office of Management, January 2021, the contents of which are hereby incorporated by reference in their entirety.

The composition can include at least one of an antimicrobial preservative and an antioxidant for improving storage stability. The composition can include at least one additional component selected from the group consisting of a therapeutic agent, a coloring agent, a preservative, a pH control agent, an antioxidant, a viscosity control agent, and an odor control agent.

A concentration of the first and second waxes in the composition can be greater than a combined concentration of other ingredients in the composition. In an embodiment, the composition can include at least about 20%, e.g., about 25%, about 30%, or about 35% beeswax. In an embodiment, the composition can include at least about 20%, e.g., about 25%, about 30%, or about 33% beeswax. In an embodiment, the combined concentration of the first and second waxes in the composition is greater than 40%.

In an embodiment, the ocular treatment composition can include about 37% to about 43% beeswax; about 35% to about 41% jojoba oil; and at least one ingredient selected from the group consisting of shea butter, caprylic/capric triglyceride, phospholipid, sodium hyaluronate, and coconut oil. In an embodiment, the composition can include at least about 5% caprylic/capric triglyceride, at least about 0.1% phospholipid, from about 0% to about 0.05% sodium hyaluronate, from about 0% to about 16% coconut oil, and from about 0% to about 16% shea butter. For example, the composition can include from about 5% to about 12% caprylic/capric triglyceride, from about 0.1% to about 2% phospholipid, from about 0% to about 0.05% sodium hyaluronate, from about 0% to about 16% coconut oil, and from about 0% to about 16% shea butter The composition can be administered to the external eyelid surface of a patient for treating or preventing a broad spectrum of ocular disorders including dry eye conditions and dry eye disease; meibomian gland dysfunction; other eyelid margin disorders and diseases; eyelid and periorbital dermatitis; inflammation; infection; and symptoms associated with these maladies. Symptoms of these diseases include pain, discomfort, itching, dryness, grittiness, burning, crusting, watery eyes, vague sensations of eyes and/or lids, and/or eye fatigue. It should be understood that the composition can treat or prevent or mitigate essentially all dry eye conditions and diseases, including temporary conditions resulting from the stresses of prolonged electronic screen viewing as well as severe dry eye disease resulting from systemic diseases, such as rheumatoid arthritis and diabetes. The external eyelid surface can include the outer skin of the upper eyelid, the outer skin of the lower eyelid, the eyelid margin, the eyelashes, or combinations of two or more thereof.

A method of treating an ophthalmologic condition can include administering a semi-solid composition to the external eyelid surface of the patient. The semi-solid composition can be the ocular treatment composition described herein, or any other suitable semi-solid ocular treatment composition. When the semi-solid composition contacts the external eyelid surface, at least a portion of the composition liquefies to provide an oily film. The oily film deposited on the external eyelid surface can move to the ocular surface in minute amounts over time. The primary mechanisms for moving the liquefied composition from the external eyelid surface to the tear film and the lipid layer are blinking, lid actions, and eye movements. In this manner, application of a semi-solid composition to the external eyelid surface can provide a continuous feed system to the ocular surface. The blinking can be voluntary or involuntary.

The composition can start to be delivered to the tear film after application. Portions of the composition can remain on the external eyelid surface, e.g., to serve as a reservoir, for delivery to the eye for preferably up to 24 hours. Once deposited on the tear film, the composition does not cause blurring, stinging or other adverse reactions. The composition can both prevent evaporation of the tear film and provide a thicker tear film to protect the nociceptors. For example, the composition can protect the nociceptors from winds of about 1 MPH to about 10-20 MPH. The composition can protect the eye from stresses resulting from insufficient blinking, e.g., reduced blinking as a result of staring at an electronic screen for lengthy periods of time.

In an optimally functioning eye, the meibomian gland secretions or sebum are continually deposited on the keratinized portion of the lid margins of the upper and lower eyelids and moved onto the ocular surface by blinking, lid actions and eye movements. The present composition can similarly enter the tear film and lipid layer once administered to the external eyelid surface. Thus, the composition can replicate the function and efficacy of natural secretions typically supplied to the eye from an optimally functionally meibomian gland upon blinking. Further, as the composition can both minimize evaporation and increase the thickness of the tear film, the composition can support the tear film such that it exceeds the protective characteristics and abilities of a normal or typical tear film. Thus, the composition can enable the ocular surface to better withstand the contemporary demands and stresses of prolonged electronic screen viewing and other visual activities associated with reduced blinking.

In an embodiment, the composition can be administered to the external eyelid surface by rubbing the composition on the external eyelid surface and, thereby, leaving the composition thereon.

As described previously, once disposed on the external eyelid surface, the residue can be moved onto the tear film and lipid layer as previously described. Thus, blinking along with lid actions and eye movements, provide a continuous mechanism for delivering the composition to the ocular surface to provide continuous protection for the aqueous layer and minimize evaporation.

Although more of the composition is delivered to the tear film and ocular surface during waking hours, it should be understood that the composition can continue to protect the ocular surface even while the patient is asleep. It has been established that although the lids may be physically shut with the upper eyelid overriding the lower eyelid to ensure closure during sleep, the eyelids may not prevent ambient air from reaching the tear film. This exposure of the tear film to ambient air during sleep can result in desiccation, compromise to the tissue of the ocular surface, discomfort, and difficulty in sleeping. The presence of the composition protects against evaporation, thus preventing desiccation and the sequelae. As such, application of the composition to the external eyelid surface can protect the ocular surfaces for about 10 hours to about 24 hours per day.

The composition can provide an extended period of protection for the ocular surfaces and neurosensory systems, including the nociceptors. For example, the composition can be administered about 1 to 4 times per day to protect the ocular surfaces for about 10 hours to about 24 hours per day. In an embodiment, the composition can be rubbed on the external eyelid surface in a back-and-forth motion from 1 to 4 times.

The composition can be provided in any suitable form to facilitate depositing the composition on the external eyelid surface. Preferably, the composition is provided in a container similar to that conventionally used for lip balms. For example, the composition can be dispensed from a conventional lip balm dispenser such as a tubular cannister or a small, wide-mouth oval or circular cannister.

In an embodiment, the composition is configured as a cylindrical bar or stick and provided in a tubular cannister to facilitate application of the composition directly on the external eyelid surface. A diameter of the cylindrical bar or stick can be about 9-17 mm and, in another embodiment, 13-15 mm. In an embodiment, the composition can be rubbed on closed eyelids by moving the tubular cannister back-and-forth motion across the entire width of the eyelids, starting on the side of each lid closest to the nose. One application or dose of the composition can include administering the composition by moving the cannister 2 to 4 times back and forth across the entire width of the eyelid. This technique is effective in delivering the treatment composition to the eyelids, eyelashes and eyelid margins. The composition can be applied in this manner 1 to 4 times per day.

In an embodiment, the composition can include from about 20% to about 45% beeswax, from about 20% to about 45% jojoba oil, from about 0% to about 16% shea butter, from about 8% to about 10% caprylic/capric triglyceride, from about 1% to about 2% phospholipid, from about 0.01% to about 0.02% sodium hyaluronate, and from about 0% to about 16% coconut oil.

In an embodiment, the composition can include about 40% beeswax, about 35% jojoba oil, about 15% shea butter, about 8.99% caprylic/capric triglyceride, about 1.00% phospholipid, and about 0.01% sodium hyaluronate.

In an embodiment, the composition can include about 37% beeswax, about 36% jojoba oil, about 16% shea butter, about 9.99% caprylic/capric triglyceride, about 1.00% phospholipid, and about 0.01% sodium hyaluronate.

In an embodiment, the composition can include about 37% beeswax, about 36% jojoba oil, about 9.99% caprylic/capric triglyceride, about 1.00% phospholipid, about 0.01% sodium hyaluronate, and about 16.0% coconut oil.

In an embodiment, the composition can include about 37% beeswax, about 36% jojoba oil, about 8% shea butter, about 9.99% caprylic/capric triglyceride, about 1.00% phospholipid, about 0.01% sodium hyaluronate, and about 8.0% coconut oil.

In an embodiment, the composition can include about 45% beeswax, about 45% jojoba oil, and about 10% caprylic/capric triglyceride.

In an embodiment, the composition can include about 45% beeswax, about 45% jojoba oil, and about 10% coconut oil.

In an embodiment, the composition can include about 45% beeswax, about 45% jojoba oil, and about 10% shea butter.

In an embodiment, the composition can include about 30% beeswax, about 30% jojoba oil, about 13% shea butter, about 15% caprylic/capric triglyceride, and about 16% coconut oil.

In an embodiment, the composition can include about 30% beeswax, about 30% jojoba oil, about 16% shea butter, about 8% caprylic/capric triglyceride, and about 16% coconut oil.

In an embodiment, the composition can include about 25% beeswax, about 25% jojoba oil, about 20% shea butter, about 15% caprylic/capric triglyceride, and about 15% coconut oil.

In an embodiment, the composition can include about 20% beeswax, about 20% jojoba oil, about 20% shea butter, about 20% caprylic/capric triglyceride, and about 20% coconut oil.

An applicator or delivery system for treating or preventing an ophthalmologic condition in a patient can include a package and an ocular treatment composition placed in the package. The ocular treatment composition in the package can be in semi-solid form when in the package and can liquefy when in contact with the external eyelid surface of the patient. In a preferred embodiment, the semi-solid composition is in the form of a generally cylindrical bar or stick and the package is a tubular cannister having a mechanism, e.g., a twistable knob or push mechanism at a bottom end thereof, that is configured to raise or lower the semi-solid composition as desired. However, other package configurations, utilizing other methods of product application, like jars, tubes, bottles, aerosols, or pouches, in which the ocular treatment composition could be placed and from which the patient could apply the composition would also be acceptable. The package can be configured for single or multiple per-day administration to the patient.

The package can include an outer container, a first product container, and a second product container within the outer container. The first product container can include the ocular treatment composition and the second product container can include a surface for labeling and facilitate product display and handling. The outer container can include an item selected from the group consisting of a single bar code, a single new drug code, and a single universal product code.

The ocular treatment composition can include from about 37% to about 43% beeswax; from about 33% to about 41% jojoba oil; and at least one ingredient selected from the group consisting of shea butter, caprylic/capric triglyceride, phospholipid, sodium hyaluronate, and coconut oil.

With subconscious blinking, minute, e.g., nanoliter or microliter amounts, of the composition can move from the eyelid surface to the eyelid margins and then across the eyelid margins to the fluid menisci where the tear film is effectively attached to the lower and upper eyelids. Blinking then distributes and mixes the composition into the appropriate layers of the tear film. The more forceful the blink, the greater the amount of composition delivered. Blinking is primarily subconscious but may be conscious. Forceful blinking may also be either conscious or subconscious depending upon the individual circumstances.

The desired therapeutic response of treatment with the composition is to increase the protection provided by the tear film to the ocular surfaces and corneal nociceptors most noticeably during the waking hours by changing the chemical composition and structure of the tear film by the use of a reservoir feed system to deliver the desired chemical constituents to the tear film and ocular surfaces without creating blurring of vision. The composition has the potential to fortify or enhance the lipid layer and the tear film to exceed the protective characteristics and abilities of a normal or typical tear film, thus enabling the ocular surface to better withstand the contemporary demands and stresses of prolonged electronic screen viewing and other visual activities associated with reduced blinking.

Increased protection of the ocular surface following administration of the composition has been demonstrated by interferometric measurements described herein, by an improvement in patient comfort, and by an improvement in stare time. Administration of the composition can provide immediate relief, delayed relief, sustained relief, or a combination thereof. The composition can be storage stable, e.g., remain homogeneous with no signs of separation or discoloration, for at least six months from time of manufacture.

The compositions described herein may be regulated as a cosmetic, drug, device, medicament, or combinations thereof. In an embodiment, the compositions can serve as a vehicle for delivering one or more drug active agents. The one or more drug active agents can include an active pharmaceutical ingredient for bringing about a therapeutic effect to the eye. Accordingly, an embodiment is directed to a pharmaceutical composition comprising the ocular treatment composition and at least one ophthalmologically or pharmacologically acceptable drug active agent.

The present teachings are illustrated by the following examples.

EXAMPLES

Example 1

Exemplary Compositions

Tables 1 and 2 provide components of exemplary compositions that were prepared.

TABLE 1

| Exemplary Composition Ingredients | 1 % W/W | 2 % W/W | 3 % W/W | 4 % W/W | 5 % W/W |
|---|---|---|---|---|---|
| White Beeswax | 40.0 | 37.0 | 37.0 | 37.0 | 45.0 |
| Jojoba oil | 35.0 | 36.0 | 36.0 | 36.0 | 45.0 |
| Shea Butter | 15.0 | 16.0 | — | 8.00 | — |
| Caprylic/Capric Triglyceride | 8.99 | 9.99 | 9.99 | 9.99 | 10.0 |
| Phospholipid | 1.00 | 1.00 | 1.00 | 1.00 | — |
| Sodium Hyaluronate | 0.01 | 0.01 | 0.01 | 0.01 | — |
| Coconut Oil | — | — | 16.0 | 8.00 | — |
| To Make | 100.0 | 100.0 | 100.0 | 100.0 | 100.0 |
| *Penetrometer Results (lb.) | — | — | — | 4.28 | 5.41 |

*As measured on a Facchini (48011 ALFONSINE, Italy) Penetrometer.

TABLE 2

| Exemplary Composition Ingredients | 6 % W/W | 7 % W/W | 8 % W/W | 9 % W/W | 10 % W/W | 11 % W/W |
|---|---|---|---|---|---|---|
| White Beeswax | 45.0 | 45.0 | 30.0 | 30.0 | 25.0 | 20.0 |
| Jojoba oil | 45.0 | 45.0 | 30.0 | 30.0 | 25.0 | 20.0 |
| Shea Butter | — | 10.0 | 13.0 | 16.0 | 20.0 | 20.0 |
| Caprylic/Capric Triglyceride | — | — | 15.0 | 8.00 | 15.0 | 20.0 |
| Phospholipid | — | — | — | — | — | — |
| Sodium Hyaluronate | — | — | — | — | — | — |
| Coconut Oil | 10.0 | — | 12.0 | 16.00 | 15.00 | 20.0 |
| To Make | 100.0 | 100.0 | 100.0 | 100.0 | 100.0 | 100.0 |
| Penetrometer Results (lb.) | 5.61 | 7.02 | 3.80 | 3.74 | 2.93 | 1.49 |

Exemplary Composition 4 was prepared by combining the white beeswax, jojoba oil, shea butter, caprylic/capric triglyceride, and coconut oil in a suitable vessel to form a mixture. The mixture was slowly warmed to 65-70° C.

Mixing was initiated once the composition became fluid. Once the composition appeared homogeneous, and while mixing, the temperature was increased to 70-75° C., and the phospholipid was slowly added. While maintaining the temperature between 70 and 75° C., mixing was continued until the phospholipid was uniformly dispersed, and the composition was homogeneous in appearance. While maintaining the temperature between 70 and 75° C., the sodium hyaluronate was added and mixing continued until the sodium hyaluronate was uniformly dispersed and the composition was homogeneous in appearance. While mixing, the composition was allowed to cool to 67-70° C. The composition was disposed in containers while maintaining the temperature of the composition at 67-70° C.

Firmness of Exemplary Compositions 4 and 5 was measured using a Facchini (48011 ALFONSINE, Italy) Penetrometer. Test batches were prepared as described above. While liquid (70-75° C.) approximately 50 grams of test batch were poured into a 2 fl. oz. PP jar. The samples were allowed to cool (solidify) in an ambient environment. Once cooled (approximately 20 minutes), a cap was applied, and the samples were permitted to stand at ambient temperature for 24-48 hrs. before testing.

To test the firmness of the samples, the test samples were placed in a constant temperature (25° C.) bath. After 30 minutes, the sample to be tested was removed from the bath and placed on the laboratory countertop. The cap was removed. Holding the jar firmly on the laboratory countertop with the left hand, the Facchini Penetrometer was held between thumb and forefinger of the right hand, push button-commanded indicator hand, the plunger was placed against the sample surface and pressed with increasing pressure until the plunger tip slowly penetrated into the sample up to the notch. The Facchini Penetrometer was removed and measurements from the "lb" scale were recorded. The plunger was thoroughly cleaned, and repeat measurements were taken at least 2 more times. The average measurement was reported.

Exemplary Compositions 1-3 and 5-11 were prepared in a manner similar to the method described for preparing Exemplary Composition 4, with slight adjustments to temperature, ingredients, and/or order of addition of ingredients. Thus, one of ordinary skill in the art would be able to prepare Exemplary Compositions 1-3 and 5-11 based on the description provided herein for Exemplary Compositions 4.

Example 2

Ocular Film Evaluation

The effectiveness of the composition identified as Exemplary Compositions 4 in Table 1 in improving the ocular film was evaluated in the clinical environment on consenting human subjects by a licensed, experienced clinician and compared to the effectiveness of a commercially available control. The study also recorded each subject's perceptions of eye comfort and blurring of vision. For convenience, the specific ingredients of the exemplary composition tested (Exemplary Compositions 4) is provided in Table 3 below.

TABLE 3

| Ingredients* | % W/W |
|---|---|
| Beeswax | 37.0 |
| Simmondsia Chinensis (Jojoba) Seed Oil | 36.0 |
| Butyrospermum Parkii (Shea) Butter | 8.0 |

TABLE 3-continued

| Ingredients* | % W/W |
|---|---|
| Cocos Nucifera (Coconut) Oil | 8.0 |
| Caprylic/Capric Triglyceride | 9.99 |
| Lecithin | 1.0 |
| Sodium Hyaluronate | 0.01 |
| Total | 100.00 |

*PCPC's INCI Dictionary Nomenclature

The control used in the evaluation was Retaine MGD by OCuSoft, Inc. (Active ingredients: light mineral oil 0.5% and mineral oil 0.5%; Inactive Ingredients: Cetalkonium chloride, glycerol, poloxamer 188, tris hydrochloride, tromethamine, tyloxapol, and water for injection).

Each subject was diagnosed to have clinically significant dry eye syndrome. The lipid layer thickness (LLT) and eye comfort level of each subject was also determined. Only subjects presenting with a LLT of ≤55 nm and a comfort score not greater than "C" at the time of study initiation were permitted to participate in the study. Subjects were instructed not to use another eye treatment product during the test period.

Each product was applied as intended. For the Control, 2 drops were instilled into the left eye ocular sac created by distending the lower lid. Exemplary Composition 4 was packaged in a lip or balm stick type container and applied to the closed eyelids of the right eye using a back-and-forth motion across the entire width of the eyelids. This study utilized 4 back-and-forth applications starting close to the nose and moving across the entire eyelid. Additional or repeat application of the test products were not permitted during the study.

Each product was measured for lipid layer thickness (LLT) and eye comfort. LLT was measured in nanometers with a LipiView® Ocular Surface Interferometer (TearScience, Morrisville, N.C.) which measures LLT by analyzing the interferometric color changes during the test period.

Eye comfort was reported by the subject using a sliding scale which described the subject's comfort level. Symptoms were rated using the scale provided in Table 4 below.

TABLE 4

Eye Comfort Scale

| Symptoms | No Problems Optimal | Satisfactory-Comfortable (not optimal but not uncomfortable) | Uncomfortable (irritating but does not interfere with my day) | Bothersome (irritating and interferes with my day) | Intolerable (unable to perform my daily tasks) |
|---|---|---|---|---|---|
| Grade | A | B | C | D | F |

Subjects were also requested to report if any blurring of vision occurred during the test period. Data were collected 0, 0.25, 0.5, 1, 2, 4, 6 and 24 hours after application.

Results

LLT and Eye Comfort results are presented in Table 5 below. No blurring was reported by subjects for either product during the test.

TABLE 5

| | Subject 1 Exemplary | | | | Subject 2 Exemplary | | | |
| --- | --- | --- | --- | --- | --- | --- | --- | --- |
| | Composition 4 | | Control | | Composition 4 | | Control | |
| Time (Hr.) | Right Eye LLT | Right Eye Comfort | Left Eye LLT | Left Eye Comfort | Right Eye LLT | Right Eye Comfort | Left Eye LLT | Left Eye Comfort |
| 0 | 47 | D | 51 | D+ | 53 | D+ | 48 | D+ |
| 0.25 | 55 | D+ | 77 | C | 56 | D+ | 64 | C |
| 0.5 | 72 | C | 64 | C+ | 64 | C− | 71 | B− |
| 1 | 82 | C+ | 54 | B− | 76 | B− | 58 | B− |
| 2 | ≥100 | B | 47 | B− | ≥100 | B− | 51 | C |
| 4 | 92 | B+ | 49 | C− | ≥100 | B+ | 42 | D+ |
| 6 | ≥100 | B+ | 42 | D+ | 96 | A− | 46 | D+ |
| 24 | 68 | C+ | 48 | D+ | 77 | B− | 45 | D+ |

DISCUSSION

For both subjects, LLT was improved at the first 15-minute evaluation. The control formula evidenced greater improvement than Exemplary Composition 4 at the 15- and 30-minute evaluations. This was expected, since the control eyedrop formula containing lipids is applied directly to the tear film, while the exemplary formula requires an initial "loading" time to reach the tear film.

At the 1-hour evaluation, the LLT for the control formula regressed toward baseline, while the LLT for Exemplary Composition 4 increased for both subjects. This was again expected since the control product film would be washed out and diluted by normal ocular activities, whereas the Exemplary Composition 4 film would continue to generate a thicker film, resist wash out, and initiate creation of a reservoir from which sustained benefits would be delivered.

At the 2-hour evaluation, the LLT for the control formula had regressed to baseline, while the LLT for Exemplary Composition 4 increased more than the capability of the instrument to measure for both subjects. (≥100 nm).

At the 4 and 6-hour evaluations, the LLT for the control formula had regressed to below baseline values, as might be expected, since LLT decreases over the course of the waking hours. The LLT for Exemplary Composition 4 remained at a high level, measuring 95 nm to ≥100 nm for both subjects.

At the 24-hour evaluation, the control formula LLT results for both subjects were essentially the same as the baseline values prior to the start of study, as were the comfort scores. Data show both LLT and comfort grades were not significantly improved by the control formula 24 hours after application.

At the 24-hour evaluation, Exemplary Composition 4 LLT results for both subjects were significantly better than baseline, exhibiting an increase in film formation and film substantivity. Comfort scores for both subjects had also demonstrated clinical improvement.

Conclusion

Exemplary Composition 4 yielded improvement in ocular film functionality and subject comfort over the 24-hour test period. Clinical evaluation also confirmed that the subject's dry eye condition improved. Exemplary Composition 4 also demonstrated continuous film formation and improvement in the subjects' eye comfort as a sustained effect when compared to a commercial product control tested in parallel.

Example 3

Stare Time Assessment

The effectiveness of the composition identified as Exemplary Composition 4 in Table 1 in improving stare times was evaluated in the clinical environment on consenting human subjects by a licensed, experienced clinician and compared to the effectiveness of a commercially available control. The test room was maintained at a relative humidity level of 30% to 40%. Subjects were instructed as to the purpose of the stare time test, the plan of the study, and the necessity to maintain fixation at the target object. Subjects were advised that each eye would be treated. The subject was seated and asked to look at a target object 2 to 6 feet from the eyes at or not more than 30 degrees below eye level. Subjects were instructed to shut their eyes down fully, but not to squeeze and, after opening, to stare at the target object for as long as possible without blinking. A computer screen displaying an object for fixation was utilized. The examiner provided an approximate 30-60 second rest period and then instructed the subject to shut the eyelids fully and stare at the target until forced to blink. A stopwatch was used to measure the stare time in seconds. A stare time ≤7 seconds was required to be admitted to the study. The test product, Exemplary Composition 4, was used on the right eye of both subjects, and the commercial product on the left. The commercial product tested was Retaine MGD. The test evaluated the treatments effects initially (time zero) and then at 1, 3 and 5 hours thereafter. Eye comfort was reported by the subject using the sliding scale shown in Table 4.

The results are provided in tabular form as follows:

TABLE 6

| | SUBJECT 3 | | | | | | SUBJECT 4 | | | | | |
| --- | --- | --- | --- | --- | --- | --- | --- | --- | --- | --- | --- | --- |
| | Example 4 | | | Control | | | Example 4 | | | Control | | |
| Hour | Stare time (sec) | Comfort | Hour | Stare time (sec) | Comfort | Hour | Stare time (sec) | Comfort | Hour | Stare time (sec) | Comfort |
| Zero | 6 | D | Zero | 5 | D | Zero | 7 | D | Zero | 6 | D |
| 1 | 11 | C | 1 | 6 | D | 1 | 13 | D | 1 | 8 | D |
| 3 | 22 | B | 3 | 4 | D | 3 | 18 | B | 3 | 5 | D |
| 5 | 19 | B | 5 | 4 | D | 5 | 21 | B | 5 | 7 | D |

DISCUSSION

When the tear film is inadequate or compromised, blinking occurs to restore the tear film and to provide protection for the neuro sensory system of the ocular surface. While the number of blinks and the time between blinks varies across patients, the length of time one stares without blinking can be measured. The length of time one stares is a metric to evaluate a patient's dry eye condition.

The time between blinks is termed the interblink interval (IBI). It is approximately 2.5 seconds for those with dry eye and approximately 6 seconds for those without dry eye. (Johnston et al, 2013).

Another metric to evaluate dry eye is the length of time that participants can keep their eyes open, referred to as the maximum blink interval (MBI). This test was developed to seek "a simple useful test for dry eye to minimize dependence upon dedicated reagents and machines". The MBI is approximately 10 seconds for those with dry eye and 24 seconds for those without dry eye.

An ocular dry eye treatment composition should increase both the interblink interval and the maximum blink interval. Increasing these intervals is evidence of increased protection for the ocular surfaces and the related neuro sensory system and a measurement of treatment efficacy. The longer the stare time, the less the stress on the tear film, the ocular surface and related neuro sensory system, resulting in increased eye comfort. The term stress time refers to the length of time a subject can stare without blinking from both the scientific and clinical aspects.

The study of stare time with Subject 3 and Subject 4 was conducted with the exemplary composition (Exemplary Composition 4) and a control, a commercially available dry eye product, Retaine MGD (formulae provided herein).

Conclusion

Exemplary Composition 4 yielded approximately 2.5 to 3.0 times improvement in stare time and tear film functionality over the 5-hour test period, when compared to a commercial product. Eye comfort improved from bothersome-irritating to satisfactory-comfortable over the 5-hour test period when compared to a commercial product.

The present subject matter being thus described, it will be apparent that the same may be modified or varied in many ways. Such modifications and variations are not to be regarded as a departure from the spirit and scope of the present subject matter, and all such modifications and variations are intended to be included within the scope of the following claims.

We claim:

1. An ocular treatment composition, comprising at least about 37% beeswax; at least about 36% jojoba oil; and at least one ingredient selected from the group consisting of shea butter, caprylic/capric triglyceride, phospholipid, sodium hyaluronate, and coconut oil,
wherein the composition is substantially water-free, and
wherein the composition is non-fluid at room temperature and liquefies when contacted with the skin at body temperatures.

2. The composition of claim 1, wherein the composition comprises about 37% beeswax, about 36% jojoba oil, about 16% shea butter, about 9.99% caprylic/capric triglyceride, about 1.00% phospholipid, and about 0.01% sodium hyaluronate.

3. The composition of claim 1, wherein the composition comprises about 37% beeswax, about 36% jojoba oil, about 9.99% caprylic/capric triglyceride, about 1.00% phospholipid, about 0.01% sodium hyaluronate, and about 16.0% coconut oil.

4. The composition of claim 1, wherein the composition comprises about 37% beeswax, about 36% jojoba oil, about 8% shea butter, about 9.99% caprylic/capric triglyceride, about 1.00% phospholipid, about 0.01% sodium hyaluronate, and about 8.0% coconut oil.

5. The composition of claim 1, wherein the composition comprises about 45% beeswax, about 45% jojoba oil, and about 10% caprylic/capric triglyceride.

6. A pharmaceutical composition, comprising:
the ocular treatment composition of claim 1; and
at least one drug active.

7. The composition of claim 1, wherein the composition can be storage stable for at least six months from time of manufacture.

8. A method of treating an ocular condition in a patient, comprising administering the composition of claim 1 to a patient in need thereof.

9. The method of claim 8, wherein the composition is in semi-solid form and is administered by applying the composition to the patient's external eyelid surface, leaving a sufficient quantity thereon to function as a reservoir.

10. The method of claim 9, wherein the composition is administered without causing blurring to the patient.

11. The method of claim 9, wherein the method provides immediate relief, delayed relief, sustained relief, or combinations thereof.

12. The method of claim 9, wherein a patient shows improvement to the patient's ocular surface as measured by an interferometer.

13. A delivery system for treating or protecting from an ocular condition in a patient, comprising:
a package;
an ocular treatment composition in the package which is in semi-solid form and liquefies when in contact with an external eyelid of the patient, wherein
the ocular treatment composition is the composition of claim 1,
the composition in the package is cylindrical; and
the package is a tubular cannister having a mechanism to raise or lower the composition in the cannister.

14. The delivery system according to claim 13, wherein the composition in the package is useful for single or multiple per-day administration to the patient.

15. The delivery system of claim 13, wherein the package comprises:
an outer container; and
a first product container and a second product container within the outer container,
wherein the first product container includes the ocular treatment composition; and
the second product container includes a surface for labeling.

16. The delivery system according to claim 15, wherein the outer container includes an item selected from the group consisting of a single bar code, a single new drug code and a single universal product code.

* * * * *

UNITED STATES PATENT AND TRADEMARK OFFICE
CERTIFICATE OF CORRECTION

PATENT NO. : 11,213,551 B1
APPLICATION NO. : 17/222379
DATED : January 4, 2022
INVENTOR(S) : Donald R. Korb, Karl F. Popp and John A. Shipps It is certified that error appears in the above-identified patent and that said Letters Patent is hereby corrected as shown below:

On the Title Page

Item (72) please remove the Inventor cities of "Boston, MA (US)" for Inventors 2 and 3 and replace all information for Inventors 2 and 3 with the following: "Karl F. Popp, Schodack Landing, NY(US), John A Shipps, Wrentham, MA(US)".

Signed and Sealed this
Twenty-sixth Day of July, 2022

Katherine Kelly Vidal
*Director of the United States Patent and Trademark Office*